(12) United States Patent
Peng et al.

(10) Patent No.: US 6,306,837 B1
(45) Date of Patent: Oct. 23, 2001

(54) HEAVY METAL CHELATING AGENT FOR ORAL ADMINISTRATION, ITS SYNTHESIS AND ITS USES IN MEDICINE AND HEALTH PROTECTION

(75) Inventors: Shiqi Peng; Chao Wang; Ming Zhao; Xingwei Li; Yancheng Wu; Taigang Mo, all of Sichuan (CN)

(73) Assignee: Sichuan Research Institute of Nature Drugs, Sichuan (CN)

( * ) Notice: Subject to any disclaimer, the term of this patent is extended or adjusted under 35 U.S.C. 154(b) by 0 days.

(21) Appl. No.: 09/473,737

(22) Filed: Dec. 28, 1999

(30) Foreign Application Priority Data

Dec. 29, 1998 (CN) .............................................. 98126505 A

(51) Int. Cl.[7] .......................... A61K 31/70; A61K 38/14
(52) U.S. Cl. ................................... 514/62; 514/9; 514/53; 514/836; 530/322; 536/4.1; 536/17.2; 536/17.5; 536/17.6; 536/18.5
(58) Field of Search ..................................... 536/4.1, 17.2, 536/17.5, 17.6, 18.5; 530/322; 514/2, 9, 836, 53, 62

(56) References Cited

U.S. PATENT DOCUMENTS 5,668,272 * 9/1997 Prasad et al. .
5,705,585 * 1/1998 Hogan, Jr. .
5,981,467 * 11/1999 Hogan, Jr. .
5,994,517 * 11/1999 Tso et al. .

* cited by examiner

Primary Examiner—James O. Wilson
(74) Attorney, Agent, or Firm—Jenkens & Gilchrist, a Professional Corporation

(57) ABSTRACT

The present invention relates to a new kind of heavy metal chelating agents and a preparation process and uses thereof. The said heavy metal chelating agents are expressed in α-[D(+)glucose-1-yl-amino]-β3-mercapto-(S)-propanoic acid (abbreviated to NGP,I) and/or N,N'-di[D(+)glucose-1-yl]-L-cystine (abbreviated to NGCD,II). In the process of preparation, glucose and cysteine are reacted with a base, with a reducing agent, and the obtained products are acidified to give NGP,I, which can be used in and/or as drugs, health foods and food additives for accelerating the excretion of heavy metals including Pb, Cd, Hg, Al, Sb, As, etc. The structural feature of the compounds of the present invention is that they contain glucose and cysteirie in their molecules. Compared with the heavy metal-excreting drugs of prior art, the compounds of the present invention have four advantages, namely suitability for oral administration, high ability to accelerate the excretion of heavy metals, high selectivity and less toxicity.

10 Claims, No Drawings

HEAVY METAL CHELATING AGENT FOR ORAL ADMINISTRATION, ITS SYNTHESIS AND ITS USES IN MEDICINE AND HEALTH PROTECTION

The present invention relates to a heavy metal chelating agent, in particular a new kind of oral heavy metal chelating agents comprising glucose as kinetophore and cysteine as pharmacophore, the preparation process and uses thereof.

Heavy metals, typically lead, are harmful to human body. Human beings are always affected in various ways by a variety of heavy metal pollution in daily life. For example, lead pollution exists in almost all the vivosphere of human beings, including atmospheric pollution, potable water pollution and soil pollution. Such pollution sources are introduced into human body while people take in food, inhale air, drink water and smoke, and are assimilated, then dispersed and stored in important organs, resulting in disturbing normal metabolism and poisoning. Ninety percent of lead introduced into human body disperses in the bones. The half-life period of lead in vivo is about 1460 days. Recent research indicates that intracellular lead binds to organelle and protein. The binding is observed namely at mercapto group (—SH) of protein. The amount of the accumulated lead in vivo is increasing with age. Chronic accumulation of lead in vivo leads to changes in normal physiological function of human body.

While acute lead-poisoning population mainly spreads in industrial regions where lead vapor and smoke dust are discharged, waste gas containing lead from motors affects residents in cities by chronic lead poisoning. While children casually suffer from lead poisoning due to unwittingly taking in the peeling-off paint (from toys, furniture, wall and soil, etc.) Containing lead, porcelain tableware containing lead makes anyone suffer from chronic lead poisoning.

Main symptoms of lead poisoning include anepitihyimia, insonmia, headache, dizziness, muscle and joint ache, abdominalgia, astriction, belch and metal smelling in mouth. Lead is fatally toxic to nervous system. Lead poisoning causes disturbance of cerebral cortex excitement and inhibition, malfunction of cortex-internal organs regulation, neurasthenic symptom grouping, and toxic multiple neuritis as well as toxic brain diseases.

Drugs, which are clinically administered at present, are classified into two types, amino-carboxyl compounds and mercapto compounds. The amino-carboxyl compounds include calcium disodium edetate ($CaNa_2$-EDTA), calcium trisodium dietlhylenetriaminepentaacetate ($CaNa_3$-DTPA). The mercapto compounds include penicillamine and sodium dimercaptosuccinate. These drugs can neither be orally administered nor enter the intracellular sites. What's more, they have the drawbacks of poor selectivity and high toxicity and side effects. Therefore, their applications are rigidly restricted. It is of practical significance to seek to develop a kind of heavy metal antidote which is suitable for oral administration, has less toxicity and side-effects, and is assimilated easily as well.

An object of the present invention is to provide a new kind of oral heavy metal chelating agents comprising glucose as kinetophore and cysteine as pharmacophore.

Another object of the present invention is to provide a preparation process of the said new oral heavy metal chelating agents.

A further object of the present invention is to provide the uses of the said heavy metal chelating agents.

The new oral heavy metal chelating agents of the present invention are chemically defined as α-[D(+)glucosc-1-yl-anmino]-μ-mercapto-(S)-propanoic acid (thereinafter referred to in its al)l)reviated form as NGP,I) and/or N,N'-di[D(+)glucose-1-yl]-L-cystine (thereinafter referred to in its abbreviated form as NGCD,II), their structural formnulae are respectively as follows:

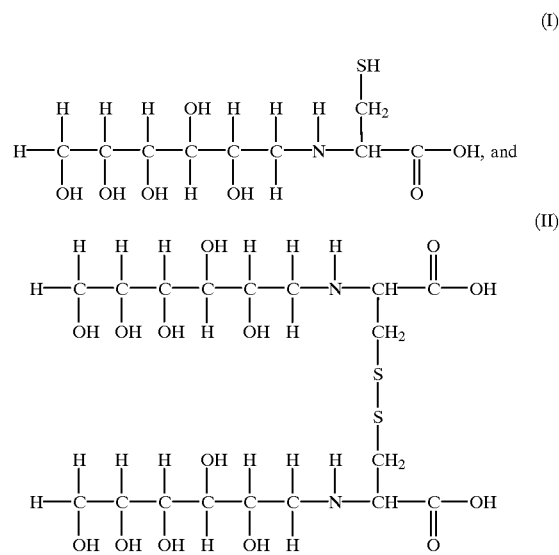

The compounds of formulae (I) and (II) are tested on animals. The result demonstrates that the compounds of the present invention significantly reduce lead content accumulated in organs and bones of mice after they are orally administered. During the period of treatment with the compounds of the present invention, lead content in feces and urine of animals increases remarkably. Therefore, the compounds of the present invention have significant abilities to accelerate the excretion of lead.

The compounds of the present invention show no effect on the concentration of iron, copper, zinc, manganese and calcium in mouse kidneys compared with control groups therefor, the compounds of the present invention can selectively excrete lead in kidney.

After the compounds of the present invention are orally administered to Kunming mice once, with a dose up to 3.0 g/kg body weight, no animal dies. Therefore, the compounds of the present invention are hypotoxic.

The compounds of the present invention show the same remarkable treatment effect in the experiments of accelerating the excretion of cadmium.

The preparation process of the new oral heavy metal chelating agent NGP,I of the present invention comprises reacting glucose and cysteine with a base, with a reducing agent, and followed by acidification to give NGP,I.

The new oral heavy metal chelating agent NGP,I of the present invention may further react with an organic base to give NGCD,II; said organic base may be N-methyl morpholine, the reaction temperature is 20–40° C., and the reaction time is 22–26 hours.

Said cysteine is one of the essential amino acids for human body. The unique mercapto group of the cysteine has a strong affinity for heavy metals. The said glucose has an ability of active transmembrane transportation. Therefore, the compounds of formulae (I) and (II) comprising glucose as kinetophore and cysteine as pharmacophore according to the present invention can accelerate the excretion of heavy metals.

In the reaction of glucose and cysteine with a base, the base can be an organic base or an inorganic base, including sodium hydroxide, potassium hydroxide, lithium hydroxide, calcium hydroxide and trimethylamine; the solvent includes methanol, water, and the reaction is conducted under the protection of nitrogen at 40–90° C. for 10–30 hours. The further reaction with a reducing agent is conducted with stirring at 30–60° C. for 3–5 days, wherein the reducing agent includes sodium borohydride, potassium borohydride and lithium aluminum hydride. And, in the subsequent acidification step, the acid can be a concentrated chlorhydric acid, phosphoric acid and acetic acid and pH is adjusted to 1–2.

The following is the specific synthetic scheme of the above reactions:

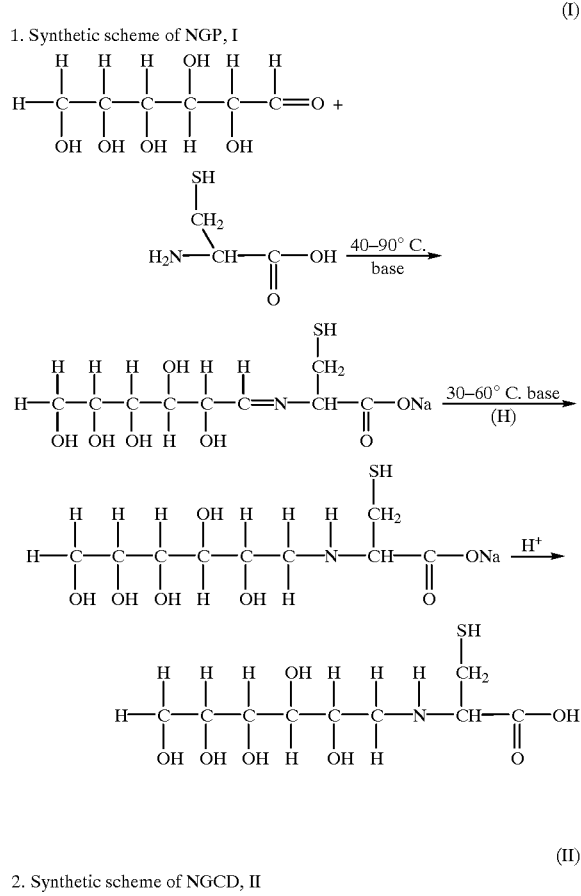

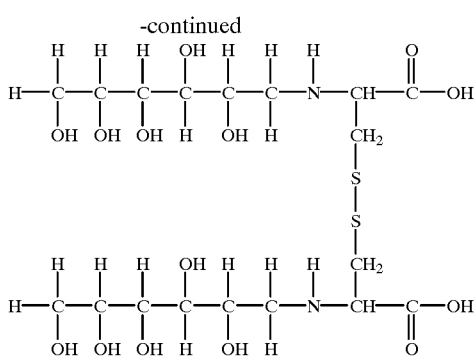

The structural feature of the compounds of the present invention is that they contain glucose and cysteine in their molecules. Compared with the heavy metal-excreting drugs of prior art, the compounds of the present invention have four advantages, that is, they are suitable for oral administration, and have high excreting ability, high selectivity and less toxicity.

The new compounds of the present invention can be used in and/or as drugs orally administered to excrete heavy metals, health foods and food additives; the compounds of the present invention can also be used in and/or as drugs orally administered to excrete lead, health foods and food additives; the compounds of the present invention can also be used in and/or as drugs orally administered to excrete cadmium, hydrargyrum, aluminum, stibonium and arsenic, health foods and food additives.

The present invention will be illustrated further by the following examples. It should be noted that these examples are merely illustrative embodiments of the present invention, and should not be construed as limitations to the scope of the present invention.

EXAMPLE 1

Synthesis of α-[D(+)glucose-1-yl-amiino]-β-mercapto-(S)-propanoic acid, i.e. NGP,I 12.1 g(0.10 mol) L-cysteinc and an inorganic base or an organic base, for example, 4.0 g(0.10 mol) sodium hydroxide, were dissolved in a protonic solvent, such as deionized water. 19.8 g(0.10 mol) D-glucose was added with stirring. Ale reaction was conducted under the protection of nitrogen at 40–90° C. for 10–30 hours, and cooled to give a syrup-like product, FAB-MS(m/e)306[M+H]$^+$, which can be used directly without further purification. Excess reducing agent, for example, 2.5 g solid sodium borohydride, was added in batches into the product with stirring at 30–60° C. for 3–5 days. Concentrated hydrochloric acid was added dropwise into the resulting syrup, and the pH was adjusted to 1–2. Undissolved substance was filtered and discarded. 100-fold deionized water was added in the filtrate, which was then adsorbed onto strong acid-type ion exchange resin (activated by an aqueous NaOH solution, type-changed by hydrochloric acid, eluted to neutral by deionized water, with a column bed volume of Φ=5.5 cm, H=15 cm). In the course of adsorption, the material solution flew through resin slowly. After the material solution passed by, the resin was washed with deionized water carefully until the effluent was around neutral. Then, the resin was washed with an organic base, for example, 3% aqueous N-methyl morpholine solution. The effluent was collected until pH=10. The residue was recrystallized from an aqueous alcohol solution after the effluent was evaporated to dryness at reduced pressure to give a white solid with a yield of 60%. M.p. 197–199° C., FAB-MS(m/e)286[M+H]$^+$. Elemental analysis; calcd. for $C_9H_{19}NO_7S$: C, 37.89; H, 6.71; N, 4.91; Found: C, 37.69; H, 6.43; N, 4.91. IR (KBr, cm$^{-1}$): 3271, 2932, 1603, 1565, 1414, 1388, 1350, 1290, 1131, 1082, 1036. $^1$H-NMR(D$_2$O) δ 3.41(m, 2H, 6-H); 3.49(m, 1H, 5-H); 3.55(dd, J=10.5, 3.6 Hz, 1H, 4-H); 3.58(t, J=2.5 Hz, 1H, 3-H); 3.90(m, 1H, 2-H); 2.95(dd, J=12.9, 8.4 Hz, 1H, 1-H); 3.09(dd, J=12.8, 3.6 Hz, 1H, 1-H); 3.72(t, J=5.1 Hz, 1H, Cys- α CH); 2.86(dd, J=9.0, 4.8 Hz, 2H, Cys-CH$_2$).

EXAMPLE 2
Synthesis of N,N'-di[D(+)glucose-1-yl]-L-cystince, i.e., NGCD,II 10 g(0.035 mol) of the product obtained in Example 1 was dissolved in deionized water. An organic base, such as N-methyl morpholine, was added and then the reaction was conducted at 20–40° C. for 24 hours. The solvent was removed under reduced pressure. The residue was recrystallized from ethanol to give a white solid, with a yield of 93%, m.p. 199–200° C., FAB-MS(m/e)567[M+H]$^+$. Elemental analysis: calcd. for $C_{18}H_{36}N_2O_{14}S_2$: C, 38.02; H, 6.38; N, 4.93; Found: C, 37.84; H, 6.40; N, 4.85. IR (KBr, cm$^{-1}$): 3271, 2930, 1610, 1566, 1416, 1382, 1351, 1290, 1130, 1080, 1031.

EXAMPLE 3
Effect of NGP,I of the Present Invention on Accelerating the Excretion of Lead in Mice 18–20 g body weight Kunming male mice were divided randomly into 5 groups. Each mouse was loaded with lead by i.p injection in a dose of 5.0 mg/kg of [Pb(CH$_3$COOH)$_2$.3H$_2$O] in 0.2 ml deionized water once per day for seven consecutive days. The mice took food and drank water ad arbitrium. After a 3-day interval, the animals of each group were administered with deionized water or a deionized water solution containing the test compound by oral gavage on the 10th day.

| Control: | deionized water |
|---|---|
| Administered groups | 0.2 mmol/kg NGP |
| | 0.4 mmol/kg NGP |
| | 0.8 mmol/kg NGP |
| Positive control: | 0.4 mmol/kg penicillamine |

The mice were administered with 0.2 ml solution/time, once a day, for 5 consecutive days. The animals were sacrificed by cervical dislocation and the kidneys, livers, femurs and brains were immediately excised 48 hours after last administration. Two hours after first administration urine was collected for 5 hours, feces of the previous day was collected after administration on the following day. Samples of urine and feces were collected as an aliquot per group per day for 5 days.

After the above samples were digested by a mixture of nitric acid: perchioric acid (3:1), they were placed in 5 ml volumetric flask, then 0.1 N HNO$_3$ was added to scratch. Lead content was measured by Varian Spectra AA-40 atomic absorption spectrophotometry (graphite furnace method).

The results were shown in Table 1 below.

TABLE 1

Evaluation of the effect on accelerating the excretion of lead in mice (X ± SD)

| | Liver μg/g (wet weight) | Kidney μg/g (wet weight) | Brain μg/g (wet weight) |
|---|---|---|---|
| Control | 6.27 ± 4.39 | 3.85 ± 4.72 | 0.38 ± 0.03 |
| NGP 0.2 mmol/kg | 5.73 ± 3.38 | 2.82 ± 0.66** | 0.28 ± 0.04$^a$ |
| NGP 0.4 mmol/kg | 3.17 ± 0.95* | 2.71 ± 1.09** | 0.23 ± 0.08$^a$ |
| NGP 0.8 mmol/kg | 3.20 ± 1.94* | 2.35 ± 0.38$^a$ | 0.22 ± 0.07$^a$ |
| Penicillamine 0.4 mmol/kg | 2.97 ± 0.94* | 2.33 ± 0.53$^a$ | 0.22 ± 0.03$^a$ |

| | Femur μg/g (wet weight) | Urine μg/g | Feces μg/g (dry weight) |
|---|---|---|---|
| Control | 31.62 ± 4.81 | 0.53 ± 0.16 | 1.23 ± 0.23 |
| NGP 0.2 mmol/kg | 25.22 ± 5.89** | 0.96 ± 0.12$^a$ | 1.81 ± 0.47* |
| NGP 0.4 mmol/kg | 24.15 ± 6.09** | 0.92 ± 0.30* | 1.80 ± 0.09$^{a,b}$ |
| NGP 0.8 mmol/kg | 21.43 ± 4.91$^a$ | 1.14 ± 0.16$^a$ | 1.92 ± 0.15$^a$ |
| Penicillamine 0.4 mmol/kg | 27.35 ± 3.42* | 1.15 ± 0.25$^a$ | 1.17 ± 0.31 |

Compared with the control, *p < 0.05, <0.01, *<0.001. Compared with the Penicillamine (positive control) at a same dose, ###p < 0.001.
$^a$corresponding to ***, $^b$corresponding to ###. n = 10 in the groups of liver, kidney, brain and femur. n = 5 in the groups of urine and feces.

EXAMPLE 4
Effect of NGP,I of the Present Invention on Accelerating the Excretion of Cadmium in Mice 18–20 g body weight Kumning male mice were injected i.p. with 3 mg/k,g CdCl$_2$.2.5H$_2$O once per day for infection for 4 days. The mice were divided randomly into 7 groups 3 days after being infected, five groups were administered by i.p. injection, and two groups were orally administered once per day for five consecutive days. The animals were killed 48 hours after last administration and kidneys were removed. The obtained samples were treated in the same way as the above lead samples were. The cadmium content was measured by HITACHI atomic absorption spectrophotometry (flame method). The results were shown in Table 2 below.

TABLE 2

Evaluation of the effect on accelerating the excretion of cadmium in mice (X ± SD)

| | Control | positive control@ | NGP(0.6 mmol/kg) | NGP(1.2 mmol/kg) | NGP(2.4 mmol/kg) |
|---|---|---|---|---|---|
| i.p. injection | 20.13 ± 0.572 | 17.42 ± 0.718* | 18.22 ± 0.166* | 14.90 ± 0.769*# | 12.47 ± 0.640* |
| Oral gavage | 60.71 ± 2.15 | — | — | — | 45.20 ± 2.83* |

@Positive control group was administered with N-acetyl-L-Cysteine, dosage was 1.2 mmol/kg; n = 8
*Compared with the control group, p < 0.05; # was compared with the positive control at the same dose, p < 0.05

EXAMPLE 5
Effect of NGP,I of the Present Invention on the Level of Other Metals in Animal Kidneys There was no significant influence on the levels of Fe, Cu, Zn, Mn, Ca in animal kidneys 5 days after administration. Tie results were shown in Table 3 below.

TABLE 3

Effect on the levels of other metals in mice kidney (X ± SD)

| | Fe | Cu | Zn | Mn | Ca |
|---|---|---|---|---|---|
| Control | 91.32 ± 19.38 | 3.37 ± 0.23 | 26.29 ± 3.23 | 1.22 ± 0.13 | 74.53 ± 9.98 |
| NGP 0.4 mmol/kg | 106.59 ± 6.04 | 3.20 ± 0.30 | 27.23 ± 4.35 | 1.19 ± 0.09 | 75.43 ± 13.51 | n = 6; the source of the samples was the same as that of excreting lead.

EXAMPLE 6

Test on Acute Toxicity of NGP,I of the Present Invention

Twenty Kunming male mice with a body weight of about 18–20 g each were administered by oral gavage with Compound (I) of the present invention once in a dose of 3.0 g/kg body weight, 0.5 ml(aqueous solution)/mouse. The administered animals were observed for 8 days, and neither abnormality nor death was found.

EXAMPLE 7

NGCD,II of the present invention was evaluated according to the methods of Examples 4, 5, 6 and 7. The results were similar to those of NGP,I.

What is claimed is:

1. A heavy metal chelating agent selected from the group consisting of α-[D(+)glucose-1-yl-amino]-β-mercapto-(S)-propanoic acid(NGP,I) and N,N'-di[D(+)glucose-1-yl-amino]-L-cystine(NGCD,II).

2. A process for preparing a heavy metal chelating agent, characterized in that glucose and cysteine are reacted with a base and with a reducing agent, and then acidified further to yield NGP,I.

3. A process according to claim 2, wherein NGP,I is further reacted with an organic base to give NGCD,II.

4. A process according to claim 2, wherein, in the reaction of glucose and cysteine with a base, said base is an organic base or an inorganic base, the reaction solvent includes methanol and water, and the reaction is conducted under the protection of nitrogen at 40–90° C. for 10–30 hours.

5. A process according to claim 4, wherein said base is selected from the group consisting of sodium hydroxide, potassium hydroxide, lithium hydroxide, calcium hydroxide, and trimethylamine.

6. A process according to claim 4, wherein the reaction with a reducing agent is conducted with stirring at 30–60° C. for 3–5 days, and said reducing agent is selected from a group consisting of sodium borohydride, potassium borohydride and lithium aluminum hydride.

7. A process according to claim 4, wherein the acidification step is conducted with an acid to attain a pH of 1–2, and said acid is selected from the group consisting of concentrated hydrochloric acid, phosphoric acid or acetic acid.

8. A method for chelating heavy metals, which comprises oral administration to a host, of the products prepared according to any one of the processes of claim 2–7.

9. A method for chelating lead, which comprises oral administration to a host, of the products prepared according to any one of the processes of claim 2–7.

10. A method for chelating cadmium, hydrargyrum, aluminum, stibonium, and arsenic, which comprises oral administration to a host, of the products prepared according to any one of the processes of claim 2–7.

* * * * *

UNITED STATES PATENT AND TRADEMARK OFFICE
CERTIFICATE OF CORRECTION

PATENT NO.    : 6,306,837 B1
DATED         : October 23, 2001
INVENTOR(S)   : Peng et al.

It is certified that error appears in the above-identified patent and that said Letters Patent is hereby corrected as shown below:

<u>Title page,</u>
Item [54], insert -- A NEW -- before "HEAVY"
Item [57], replace "β3-mercapto-" with -- β-mercapto- --
Item [57], replace "cysteirie" with -- cysteine --

<u>Column 1,</u>
Line 23, replace "namely" with -- mainly --
Line 35, replace "Containing" with -- containing --
Line 37, replace "anepitihyimia," with -- anepithymia --
Line 38, replace "insonmia" with -- insomnia --
Line 50, replace "dietlhylenetriaminepentaacetate" with
-- diethylenetriaminepentaacetate --

<u>Column 2,</u>
Lines 4-6, replace "as α-[D(+)glucosc-1-yl-anmino]-$\mu$-mercapto-(S)-propanoic acid (thereinafter referred to in its al) 1) reviated form as NGP, I)" with -- as α-[D(+) glucose-1-yl-anmino] -β-mercapto-(S)-propanoic acid (thereinafter referred to in its abbreviated form as NGP, I) --
Line 8, replace "formnulae" with -- formulae --
Line 45-46, replace "groups therefor," with -- groups. Therefore --

<u>Column 3,</u>
Line 19, replace "aluminum" with -- aluminium --

<u>Column 4,</u>
Line 31, replace "aluminum" with -- aluminium --
Line 43, replace "L-cysteinc" with -- L-cysteine --
Line 47, replace "Ale" with -- The --

<u>Column 5,</u>
Line 17, replace "L-cystince," with -- L-cystine --
Line 26, replace "caled" with -- calcd --
Line 53, replace "solution/tirne," with -- solution/time --

UNITED STATES PATENT AND TRADEMARK OFFICE
CERTIFICATE OF CORRECTION

PATENT NO. : 6,306,837 B1
DATED : October 23, 2001
INVENTOR(S) : Peng et al.

It is certified that error appears in the above-identified patent and that said Letters Patent is hereby corrected as shown below:

Column 6,
Line 32, replace "Kumning" with -- Kunming --
Lines 46-55, replace
Table 2
Evaluation of the effect on accelerating the excretion of cadmium in mice (X±SD)

|  | Control | positive control@ | NGP(0.6 mmol/kg) | NGP(1.2 mmol/kg) | NGP(2.4 mmol/kg) |
|---|---|---|---|---|---|
| i.p. injection | 20.13± 0.572 | 17.42± 0.718* | 18.22± 0.166* | 14.90± 0.769*# | 12.47± 0.640* |
| Oral gavage | 60.71± 2.15 | -- | -- | -- | 45.20± 2.83* | with

Table 2
Evaluation of the effect on accelerating the excretion of cadmium in mice (X±SD)

|  | Control | positive control@ | NGP(0.6 mmol/kg) | NGP(1.2 mmol/kg) | NGP(2.4 mmol/kg) |
|---|---|---|---|---|---|
| i.p. injection | 20.13 ±0.572 | 17.42 ±0.718* | 18.22 ±0.166* | 14.90 ±0.769*# | 12.47 ±0.640* |
| Oral gavage | 60.71 ±2.15 | -- | -- | -- | 45.20 ±2.83* |

UNITED STATES PATENT AND TRADEMARK OFFICE
CERTIFICATE OF CORRECTION

PATENT NO. : 6,306,837 B1
DATED : October 23, 2001
INVENTOR(S) : Peng et al.

It is certified that error appears in the above-identified patent and that said Letters Patent is hereby corrected as shown below:

<u>Column 6, contd.</u>
Line 66, replace "Tie" with -- The --

Signed and Sealed this

Eighteenth Day of June, 2002

Attest:

JAMES E. ROGAN
Attesting Officer       Director of the United States Patent and Trademark Office